United States Patent [19]

Gruber

[11] Patent Number: 5,026,881

[45] Date of Patent: Jun. 25, 1991

[54] PROCESS FOR THE PRODUCTION OF EPOXIDIZED FATTY ALCOHOLS

[75] Inventor: Bert Gruber, Bedburg, Fed. Rep. of Germany

[73] Assignee: Henkel Kommanditgesellschaft auf Aktien, Duesseldorf-Holthausen, Fed. Rep. of Germany

[21] Appl. No.: 179,171

[22] Filed: Apr. 8, 1988

[30] Foreign Application Priority Data

Apr. 10, 1987 [DE] Fed. Rep. of Germany ....... 3712183

[51] Int. Cl.$^5$ .......................................... C07D 301/12
[52] U.S. Cl. ................................................... 549/531
[58] Field of Search .................................. 549/231, 531

[56] References Cited

U.S. PATENT DOCUMENTS

| | | | |
|---|---|---|---|
| 2,485,160 | 10/1949 | Niederhauser et al. | 260/348 |
| 2,833,787 | 5/1958 | Carlson et al. | 549/531 |
| 3,293,269 | 12/1966 | Wolgemuth | 549/531 |

FOREIGN PATENT DOCUMENTS

| | | |
|---|---|---|
| 3002785 | 1/1980 | Fed. Rep. of Germany . |
| 0033110 | 1/1981 | Fed. Rep. of Germany . |
| 3002861 | 12/1981 | Fed. Rep. of Germany . |
| 3320219.2 | 5/1984 | Fed. Rep. of Germany . |

OTHER PUBLICATIONS

Swern, Organic Peroxides, vol. II, p. 360.

*Primary Examiner*—Frederick E. Waddell
*Assistant Examiner*—Amelia A. Owens
*Attorney, Agent, or Firm*—Ernest G. Szoke; Wayne C. Jaeschke; Henry E. Millson, Jr.

[57] ABSTRACT

In the production of epoxidized fatty alcohols by reaction of fatty alcohols containing at least one olefinic double bond with hydrogen peroxide and formic acid, the formation of secondary products is reduced by carrying out the epoxidation in the presence of a buffer.

10 Claims, No Drawings

PROCESS FOR THE PRODUCTION OF EPOXIDIZED FATTY ALCOHOLS

BACKGROUND OF THE INVENTION

1. Field of the Invention

This invention relates to a process for the production of epoxidized fatty alcohols.

2. Statement of Related Art

The conventional process for the production of epoxides from organic compounds containing at least one olefinic double bond is based on the so-called Prileschajew reaction, i.e. epoxation with percarboxylic acids (cf. D. Swern, Organic Peroxides, Vol. II, Wiley Interscience, 1971, pages 355-533).

In the practical application of this process, the percarboxylic acids are not generally used as starting materials; instead, the corresponding carboxylic acids are combined with hydrogen peroxide to form percarboxylic acids which react in situ with the olefinic double bonds. The carboxylic acids used are, for example, formic acid, acetic acid and higher homologs thereof. Catalysts, for example sulfuric acid and other mineral acids, are often used to accelerate the reaction. Although these catalysts do accelerate the reaction, they have the disadvantage that they also initiate secondary reactions including opening the oxirane ring.

Performic acid formed in situ from formic acid and hydrogen peroxide is often used for the epoxidation of olefinically unsaturated organic compounds. This system has the advantage that the formation of the percarboxylic acid does not require a catalyst. However, in view of the fact that formic acid is a stronger acid than the other carboxylic acids used for the in situ epoxidation reaction, there is an increased tendency here toward unwanted opening of the oxirane ring (cf. D. Swern, loc. cit., pages 400-401).

The epoxidation of olefinic double bonds carried out in the absence of catalysts with performic acid formed in situ is preferably used in the production of epoxides from olefins and triglycerides containing unsaturated fatty acids (cf. German Application 30 02 861 and U.S. Pat. No. 2,485,160).

The application of the epoxidation process known from the cited prior art using performic acid formed in situ to the production of epoxidized fatty alcohols gives unsatisfactory results. In addition to the secondary reactions mentioned above, unwanted formic acid esters are formed, leaving the epoxidized fatty alcohol with an unsaturated (high) saponification value.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that the non-catalyzed epoxidation of unsaturated fatty alcohols with in situ performic acid gives epoxidized fatty alcohols with lower contents of secondary products provided the epoxidation is carried out in the presence of a buffer. In addition to a high percentage of epoxide groups, the epoxidized fatty alcohols produced in accordance with the invention show distinctly reduced saponification values.

Accordingly, the present invention relates to a process for the production of epoxidized fatty alcohols by reaction of fatty alcohols containing at least one olefinic double bond with a mixture of formic acid and an aqueous solution containing 60-92% by weight hydrogen peroxide in the absence of catalysts at 40°-70° C. using 1.1-3.5 moles of hydrogen peroxide and 0.05-1 mole of formic acid per mole of double bond to be epoxidized, and wherein the epoxidation is carried out in the presence of 1-10% by weight, based on hydrogen peroxide solution (calculated as a 70% solution), of a buffer.

Suitable starting materials are $C_8$–$C_{22}$ fatty alcohols containing at least one olefinic double bond, more especially $C_{16}$–$C_{22}$ fatty alcohols of the type obtainable from natural fats and oils by known methods of fatty alcohol synthesis. These fatty alcohols are generally not used as individual chemical entities, but instead as mixtures. Preferred starting materials are oleyl alcohols which, in addition to the monounsatuated $C_{18}$ fatty alcohol present in quantities of approximately 70-90% by weight, also contain polyunsaturated $C_{18}$ fatty alcohols and, in small quantities, saturated fatty alcohols. However, unsaturated fatty alcohols or fatty alcohol fractions from rapeseed oil or fish oil which contain an increased percentage of $C_{20}$–$C_{22}$ fatty alcohols can also be epoxidized by the process of the invention.

The formic acid required for the process of the invention is normally used in the form of aqueous solutions containing at most 30% by weight water.

Buffers suitable for use in the process of the invention are, in general, salts of slightly to moderately strong acids ($pK_s$ equal to or greater than 2) which are inert to the epoxidizing agent. They are preferably used in a quantity of 3-8% by weight, based on hydrogen peroxide solution (calculated as a 70% solution).

Preferred buffers for the process of the invention include the acetates and formates of lithium, sodium, potassium, calcium, barium and zinc, hydrogen phosphates of sodium and potassium, and alkali metal oxalates, more especially sodium and potassium oxalate. Particularly preferred buffers include sodium acetate, potassium acetate, and secondary sodium phosphate.

To carry out the epoxidation reaction, a mixture of unsaturated fatty alcohol, formic acid, and buffer can be initially introduced and hydrogen peroxide subsequently added.

According to another preferred embodiment of the invention, the unsaturated fatty alcohol and formic acid are initially introduced and a buffer-containing hydrogen peroxide solution subsequently added.

The epoxidized fatty alcohols produced by the process of the invention are known compounds of commercial importance. They can, for example, be converted into polyols by reaction of the epoxide ring with mono- or polyhydric alcohols or water in known manner. These polyols are valuable intermediates in the synthesis of polyurethane resins.

The invention is illustrated but not limited by the following examples.

EXAMPLE I 135.0 g technical oleyl alcohol (Ocenol ®90/95; iodine value 94) were mixed with 16.2 g 85% formic acid, followed after heating to 65° C. by the dropwise addition of a solution of 3.65 g sodium acetate in 73.0 g 70% hydrogen peroxide. After a reaction time of 2.5 hr at 65°-70° C., the reaction mixture was washed with water until neutral and the epoxide dried in vacuo.

The epoxidized oleyl alcohol obtained had an epoxide oxygen content of 4.2% for an iodine value of 9 and a saponification value of 27.

EXAMPLES 2 to 11

The reaction was carried out under the same conditions as in Example 1. The quantities of oleyl alcohol, formic acid, hydrogen peroxide and buffers used, the reaction times and the epoxide content, the iodine values and saponification values of the epoxides obtained are shown in the following Table. The Table also includes a comparison test in which no buffer was used. The product obtained had a saponification value of 50 for an epoxide content of 3.5% and an iodine value of 4, i.e. comparing these values with those of the Examples shows that the formation of secondary products was considerably reduced by the use of buffers in accordance with the invention.

TABLE 1

Summary of the Examples

| Example no. | Ocenol 90/95 (moles) | HCOOH (85%) (moles) | $H_2O_2$ (70%) (moles) | Buffer (%, based on $H_2O_2$ solution) | Reaction time (h) | % epoxide | Iodine value | Saponification value |
|---|---|---|---|---|---|---|---|---|
| 1 | 1 | 0.6 | 3.0 | 5% $CH_3COONa$ | 2.5 | 4.2 | 9 | 27 |
| 2 | 1 | 0.3 | 1.5 | 1% $CH_3COONa$ | 5.5 | 3.2 | 17 | 35 |
| 3 | 1 | 0.3 | 1.5 | 3% $CH_3COONa$ | 5.5 | 3.5 | 19 | 27 |
| 4 | 1 | 0.3 | 1.5 | 5% $CH_3COONa$ | 5.5 | 3.3 | 27 | 24 |
| 5 | 1 | 0.45 | 2.0 | 3% $CH_3COONa$ | 3.25 | 3.9 | 10 | 34 |
| 6 | 1 | 0.45 | 2.0 | 4% $CH_3COONa$ | 3.0 | 3.9 | 12 | 29 |
| 7 | 1 | 0.45 | 2.0 | 5% $CH_3COONa$ | 5.5 | 3.8 | 16 | 24 |
| 8 | 1 | 0.3 | 3.0 | 5% $CH_3COONa$ | 5.0 | 2.8 | 40 | 13 |
| 9 | 1 | 0.45 | 3.0 | 5% $CH_3COONa$ | 5.5 | 3.6 | 25 | 15 |
| 10 | 1 | 0.6 | 3.0 | 5% $Na_2HPO_4$ | 1.5 | 4.1 | 6 | 34 |
| 11 | 1 | 0.6 | 3.0 | 5% $CH_3COOK$ | 3.0 | 4.0 | 12 | 22 |
| Comparison | 1 | 0.6 | 3.0 | — | 2.0 | 3.5 | 4 | 50 |

I claim:

1. A process for the preparation of an epoxidized fatty alcohol comprising the steps of
    A. reacting a fatty alcohol containing at least one olefinic double bond with formic acid and an aqueous solution containing from about 60 to about 92% by weight hydrogen peroxide, in the absence of any catalyst at a temperature in the range of from about 40° to about 70° C. in the presence of from about 1 to about 10% by weight of a buffer, based on the weight of aqueous hydrogen peroxide calculated as 70% aqueous solution, wherein from about 1.1 to about 3.5 moles of hydrogen peroxide and from about 0.05 to about 1 mole of formic acid are present per mole of double bond to be epoxidized, to form a reaction mixture containing the epoxidized fatty alcohol, and
    B. isolating the resulting epoxidized fatty alcohol from the reaction mixture.

2. The process of claim 1 wherein the buffer is present in a quantity of from about 3 to about 8%.

3. The process of claim 1 wherein the buffer is a salt of an acid having a $pK_s$ equal to or greater than 2.

4. The process of claim 3 wherein the buffer is at least one of an acetate or formate of lithium, sodium, potassium, calcium, barium or zinc, a hydrogen phosphate of sodium or potassium, or an alkali metal oxalate.

5. The process of claim 4 wherein the buffer is sodium acetate, potassium acetate, or secondary sodium phosphate.

6. The process of claim 1 wherein in step A the buffer-containing hydrogen peroxide solution is added to a mixture of the unsaturated fatty alcohol and the formic acid.

7. The process of claim 1 wherein in step A the unsaturated fatty alcohol is at least one $C_8$–$C_{22}$ fatty alcohol containing at least one olefinic double bond obtained from a natural fat or oil.

8. The process of claim 1 wherein in step A the unsaturated fatty alcohol is at least one $C_{16}$–$C_{22}$ fatty alcohol containing at least one olefinic double bond obtained from a natural fat or oil.

9. The process of claim 1 wherein in step A the unsaturated fatty alcohol is a technical grade alcohol containing from about 70 to about 90% by weight monounsaturated $C_{18}$ fatty alcohol, with the remainder polyunsaturated $C_{18}$ fatty alcohols and a small quantity of saturated fatty alcohols.

10. The process of claim 1 wherein in step A the aqueous solution contains from about 70 to about 92% by weight of hydrogen peroxide and formic acid.

* * * * *